(12) United States Patent
Kubota

(10) Patent No.: US 7,210,517 B2
(45) Date of Patent: May 1, 2007

(54) DIE CASTING MACHINE

(75) Inventor: Shoukou Kubota, Kanagawa (JP)

(73) Assignee: Toshiba Kikai Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/887,906

(22) Filed: Jul. 12, 2004

(65) Prior Publication Data

US 2004/0256074 A1 Dec. 23, 2004

Related U.S. Application Data

(62) Division of application No. 10/078,164, filed on Feb. 20, 2002, now Pat. No. 6,808,008.

(30) Foreign Application Priority Data

| Feb. 20, 2001 | (JP) | ............................. 2001-044083 |
| Feb. 20, 2001 | (JP) | ............................. 2001-044084 |
| Feb. 20, 2001 | (JP) | ............................. 2001-044085 |

(51) Int. Cl.
*B22D 17/22* (2006.01)

(52) U.S. Cl. ..................................... 164/312; 164/347

(58) Field of Classification Search ................ 164/113, 164/131, 347, 312
See application file for complete search history.

(56) References Cited

U.S. PATENT DOCUMENTS

| 2,785,448 | A |   | 9/1957 | Hodler |  |
| 3,752,213 | A | * | 8/1973 | Miki | ........................... 164/113 |
| 3,918,868 | A | * | 11/1975 | Villaume | ..................... 425/169 |
| 3,938,585 | A | * | 2/1976 | Rader | .......................... 164/347 |
| 4,762,163 | A |   | 8/1988 | Takehisa et al. | ............... 167/72 |
| 4,852,634 | A |   | 8/1989 | Kawai et al. | ................. 164/457 |
| 4,989,663 | A | * | 2/1991 | Kitamura | ...................... 164/312 |
| 5,433,263 | A | * | 7/1995 | Ohnishi et al. | .............. 164/347 |
| 5,915,453 | A | * | 6/1999 | Tremblay et al. | ........... 164/347 |
| 6,186,216 | B1 | * | 2/2001 | Bolde et al. | .................. 164/131 |
| 6,308,766 | B1 | * | 10/2001 | Thurner | ........................ 164/61 |
| 6,513,568 | B1 |   | 2/2003 | Wyser | ......................... 164/305 |

FOREIGN PATENT DOCUMENTS

| DE | 42 39 832 |   | 6/1994 |
| JP | 62-93056 | * | 4/1987 |
| JP | 62-114756 |   | 5/1987 |
| JP | 1-60759 |   | 4/1989 |
| JP | 1-163010 | * | 6/1989 |
| JP | 01-180767 |   | 7/1989 |
| JP | 5-24080 | * | 2/1993 |
| JP | 05-123845 |   | 5/1993 |
| JP | 5-212528 |   | 8/1993 |
| JP | 07-047457 |   | 2/1995 |
| JP | 10-314918 |   | 12/1998 |

* cited by examiner

*Primary Examiner*—Kuang Y. Lin
(74) *Attorney, Agent, or Firm*—Pillsbury Winthrop Shaw Pittman, LLP

(57) ABSTRACT

A die casting machine capable of reducing the pressure in a die cavity to a lower level such as a substantially perfect vacuum, having a movable die and a fixed die, a vacuum pump for reducing pressure in a cavity formed between the dies, and an injection apparatus for injecting and filling molten metal into the cavity with reduced pressure, at least one of the dies having an evacuation path connected with the vacuum pump and communicated with the cavity, a valve element for opening and shutting the evacuation path, and an electromagnetic driving means for making the valve element move linearly in the opening and shutting direction by electromagnetic force.

4 Claims, 11 Drawing Sheets

DIE CASTING MACHINE

CROSS-REFERENCE TO RELATED APPLICATIONS

This is a Divisional Application of U.S. application Ser. No. 10/078,164, filed Feb. 20, 2002 now U.S. Pat. No. 6,808,008, which is based upon and claims the benefit of priority from the prior Japanese Patent Application Nos. 2001-044083, filed Feb. 20, 2001, 2001-044084, filed Feb. 20, 2001 and 2001-044085, filed on Feb. 20, 2001, the entire contents all of which are incorporated herein by reference.

BACKGROUND OF THE INVENTION

1. Field of the Invention

The present invention relates to a die casting machine using vacuum die casting, that is, die casting in a state with pressure in the cavity reduced.

2. Description of the Related Art

A die casting machine is provided with a pair of dies, a fixed die plate and a movable die plate for holding these dies, a clamping apparatus for clamping the dies, an injection apparatus for injecting molten metal into a cavity formed between the dies, a molten metal supplying apparatus for supplying the molten metal to the injection apparatus, and so on. In such a die casting machine, a die casting is obtained by clamping the dies, supplying molten metal into a sleeve of the injection apparatus, injecting the molten metal into the cavity, and filling the cavity with the molten metal.

One of the causes of uneven quality of die castings is the inclusion of gas in the die castings. That is, molten metal injected into the cavity and filled in the cavity at a high speed and under a high pressure forms a turbulent flow in the sleeve and the cavity. Due to this, gas such as air or vaporized parting agent is mixed into the molten metal.

In order to overcome the above problem, there is known the vacuum casting method for decreasing the inclusion of gas and reducing unevenness of die castings caused by the inclusion.

In a die casting machine using the vacuum casting method, as disclosed for example in U.S. Pat. No. 2,785,448, the inclusion of gas into the molten metal is suppressed by injecting the molten metal into the cavity and filling the cavity with the molten metal in a state with the pressure reduced by a vacuum pump.

In the above die casting machine using vacuum casting, in order to cast a product with a high strength and high quality, it is required to be able to create a higher vacuum in the cavity and maintain the vacuum state.

If the cavity is not made a high vacuum, it is difficult to obtain enough of an effect by the vacuum die casting, because gas becomes included in the casting and distortion or a deformation of the product easily occurs when annealing or otherwise heat treating the product after casting.

In order to cast a product with a higher strength and a higher quality, specifically, it is desired to reduce the pressure in the cavity to several tens of Torr.

Further, from the viewpoint of improving the productivity of a die casting machine, it is required to shorten the time required for evacuation by the vacuum pump as far as possible.

SUMMARY OF THE INVENTION

An object of the present invention is to provide a die casting machine using vacuum casting capable of achieving a higher vacuum in the cavity.

According to a first aspect of the present invention, there is provided a die casting machine comprising a movable die and a fixed die, a vacuum pump for reducing pressure in a cavity formed between the dies, and an injection apparatus for injecting and filing molten metal into the cavity at a reduced pressure, at least one of the dies including an evacuation path connected with the vacuum pump and communicated with the cavity, a valve element for opening and shutting the evacuation path, and an electromagnetic driving means for making the valve element move linearly in the opening and shutting direction by electromagnetic force.

In the first aspect according the present invention, since an electromagnetic driving means is used for driving the valve element for opening and shutting the evacuation path formed in the die, it becomes possible to rapidly move the valve element.

Further, in the first aspect of the present invention, the valve element may be arranged between the parting faces and form a valve seat portion integrally with a die. Due to this, it becomes possible to reliably open and shut the evacuation path.

According to a second aspect of the present invention, there is provided a die casting machine comprising a movable die and a fixed die, a vacuum pump for reducing pressure in a cavity formed between the dies, an injection apparatus for injecting and filing molten metal into the cavity with a reduced pressure, an ejecting pin, for ejecting a product formed in the cavity, inserted into an insertion hole formed in a die and communicated with the cavity, a sealing member for sealing between the ejecting pin and the insertion hole to prevent air from flowing into the reduced pressure cavity, and a temperature rise prevention means for preventing a rise in the temperature of the ejecting pin due to contact with the formed product.

In the second aspect according the present invention, the temperature rise prevention means is provided to prevent a sealing member such as an O-ring from being damaged by heat.

Due to this, it becomes possible to keep the cavity sealed reliably by the sealing member and prevent air from flowing in and to create a high vacuum in the cavity.

According to a third aspect of the present invention, there is provided a die casting machine comprising a movable die and a fixed die, a vacuum pump for reducing pressure in a cavity formed between the dies, and an injection apparatus for injecting and filing molten metal into the cavity with a reduced pressure, at least one of the dies including an evacuation path connected with the vacuum pump and communicated with the cavity, a plurality of valve elements for opening and shutting the evacuation path, a plurality of electromagnetic driving means for moving the valve elements linearly in the opening and shutting direction by electromagnetic force, and a control means for independently controlling the drive operations of the electromagnetic means.

In the third aspect according the present invention, by independently controlling a plurality of electromagnetic means, it becomes possible to shorten the time required to create a high vacuum in the cavity.

BRIEF DESCRIPTION OF THE DRAWINGS

These and other objects and features of the present invention will become clearer from the following description of the preferred embodiments given with reference to the accompanying drawings, in which.

DESCRIPTION OF THE PREFERRED EMBODIMENTS

Below, preferred embodiments will be described with reference to the accompanying drawings.

First Embodiment

Figure 1:
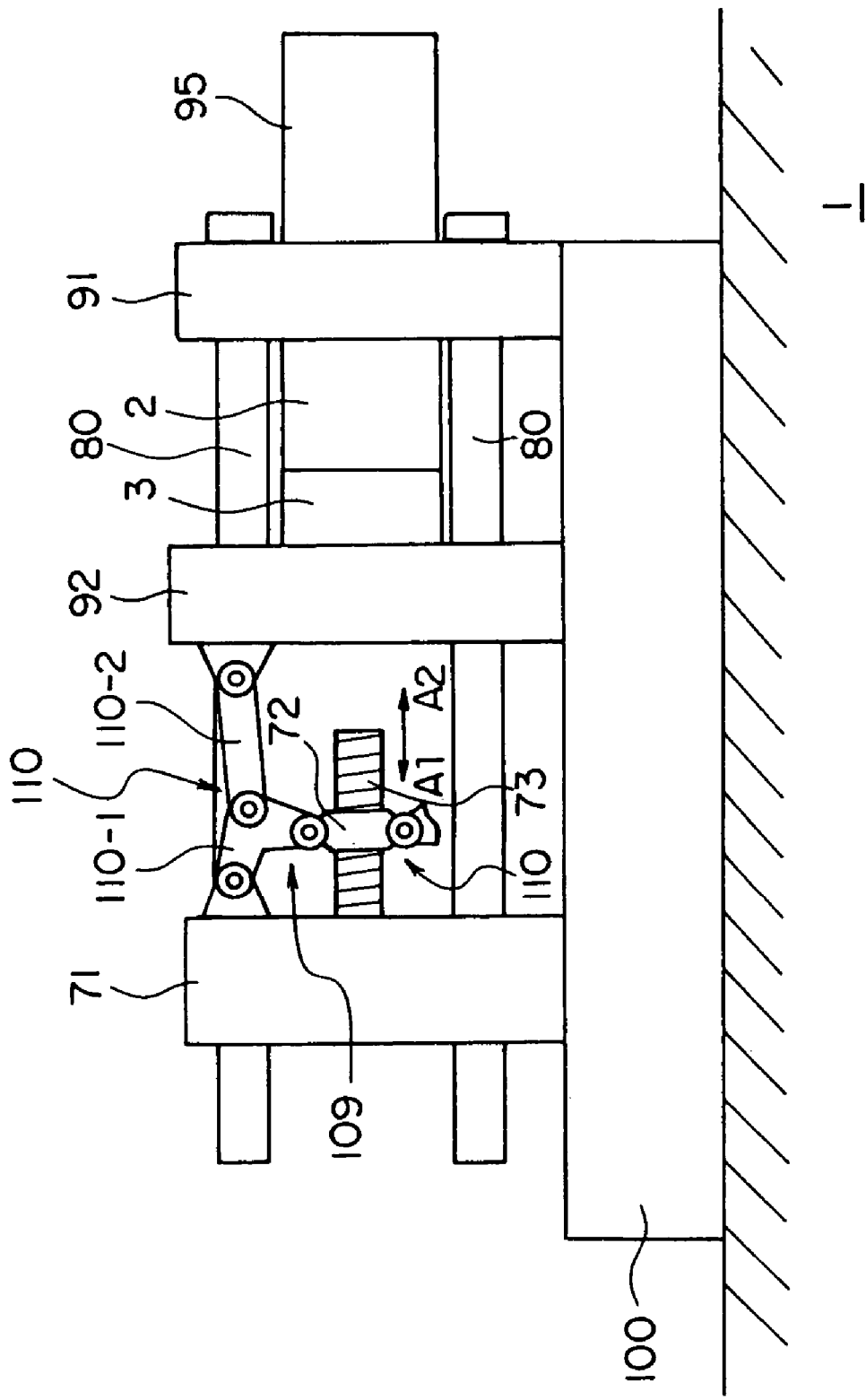
FIG. 1 is a view of an example of the configuration of a die casting machine to which the present invention is applied.

FIG. 1 is a view of an example of the configuration of the die casting machine to which the present invention is applied.

In FIG. 1, the die casting machine 1 is provided with a base 100, a fixed die plate 91 arranged on the base 100, a fixed die 2 attached to the fixed die plate 91, an injection apparatus 95 arranged on the opposite side of the fixed die plate 91 from the fixed die 2, a movable die plate 3 arranged on the base 100 facing the fixed die 2, a movable die 3 attached to the movable die plate 3 facing the fixed die 2, a link housing 71 connected to the fixed die plate 91 by tie bars 80 through the movable die plate 92, and a toggle die clamping mechanism 109 consisting of a plurality of links which connects the link housing 71 and the movable die plate 92.

The fixed die plate 91 is fixed on the base 100, while the movable die plate 92 is arranged movably on the base 100.

The link housing 71 and the fixed die plate 91 are connected by a plurality of tie bars 80 which pass through the movable die plate 92. Normally, there are four tie bars.

The toggle die clamping mechanism which connects the link housing 71 and the movable die plate 51 is provided with two pairs of link systems 110, only one of which is shown in detail in FIG. 1. FIG. 1 shows the configuration of one of the pairs in detail. Each of link systems is provided with an angled first link 110-1 and a straight second link 110-2. The first link 110-1 has an end pivoted to the link housing 71 and another end pivoted to a cross head 105. The second link 110-2 has an end pivoted to the first link 110-1 at a location between the pivot points to the link housing 71 and the cross head 105 and another end pivoted to the movable die plate.

This cross head 72 pivoted to the first link 110-1 of the toggle die clamping mechanism 109 is moved in a direction as shown by arrows A1 and A2 along the screw shaft 106, whereby the toggle die clamping mechanism 109 operates and causes the link housing 71 to be moved to or moved away from the movable die plate 92.

The screw shaft 73 is driven by a not illustrated servo motor arranged at the link housing 71. By the rotation of the screw shaft 73, the cross head 72 engaged with the screw shaft 73 is moved in the direction as shown by the arrows A1 and A2.

As shown in FIG. 1, when the cross head 72 is moved in the direction as shown by the arrow A2 by driving the not illustrated servo motor, the toggle die clamping mechanism 109 is operated and the movable die plate 92 is moved in the direction away from the link housing 71 to close the fixed die and movable die. Further movement of the cross head 72 in the direction of the arrow A2 causes the tie bars 80 to be tensioned and the fixed die 2 and the movable die 3 to be clamped.

The injection apparatus 95 injects and fills molten metal into a not illustrated cavity formed between the clamped fixed die and-movable die. By solidification of the molten metal injected into and filling the cavity, a die casting can be obtained.

Figure 2:
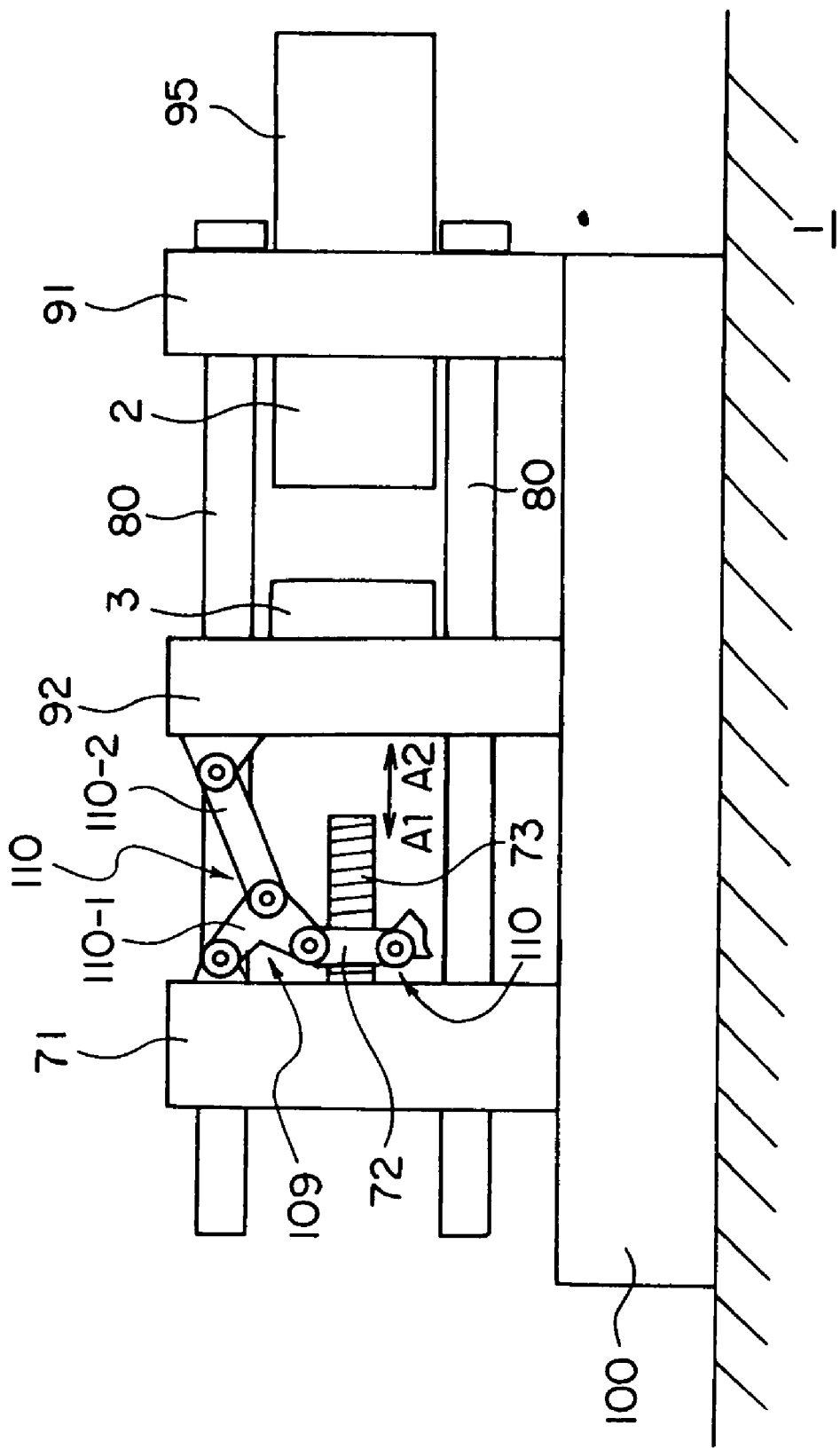
FIG. 2 is a view of a die-opening state of the die casting machine shown in FIG. 1.

On the other hand, when taking out the die casting from the dies after casting, as shown in FIG. 2, the cross head 72 is moved in the direction of the arrow A1. This causes the movable die plate 92 to be moved in a direction toward the link housing 71, i.e., the die opening direction, so that the movable die plate 3 is opened from the fixed die plate 2. When opening the movable die 3 from the fixed die 2, the die casting is moved together with the movable die 3. This die casting stuck in the movable die 3 is pushed out and ejected from the movable die 3 by the ejecting mechanism explained below.

Figure 3:
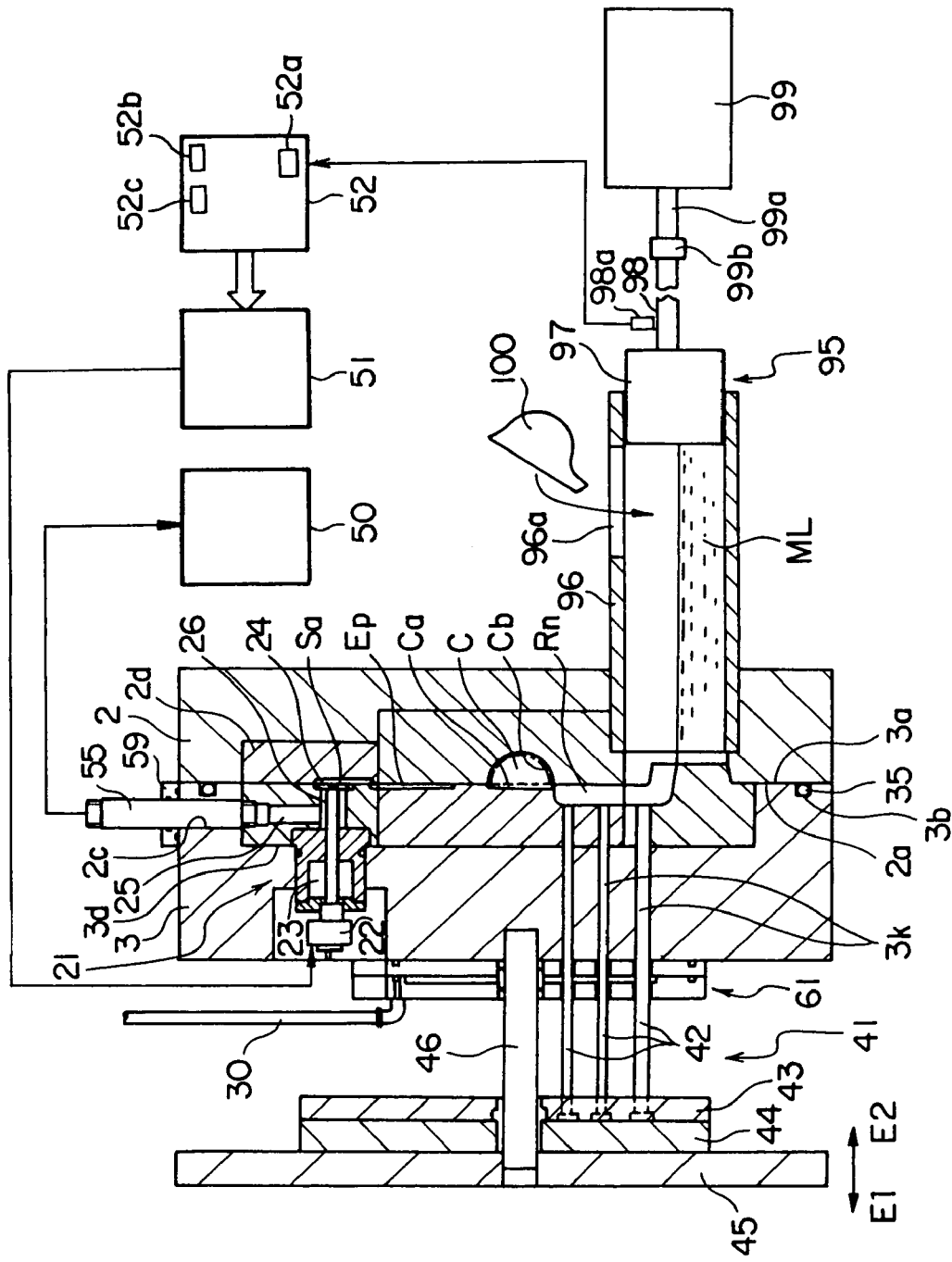
FIG. 3 is a view of the configuration around the dies according to the first embodiment of the present invention.
Figure 4:
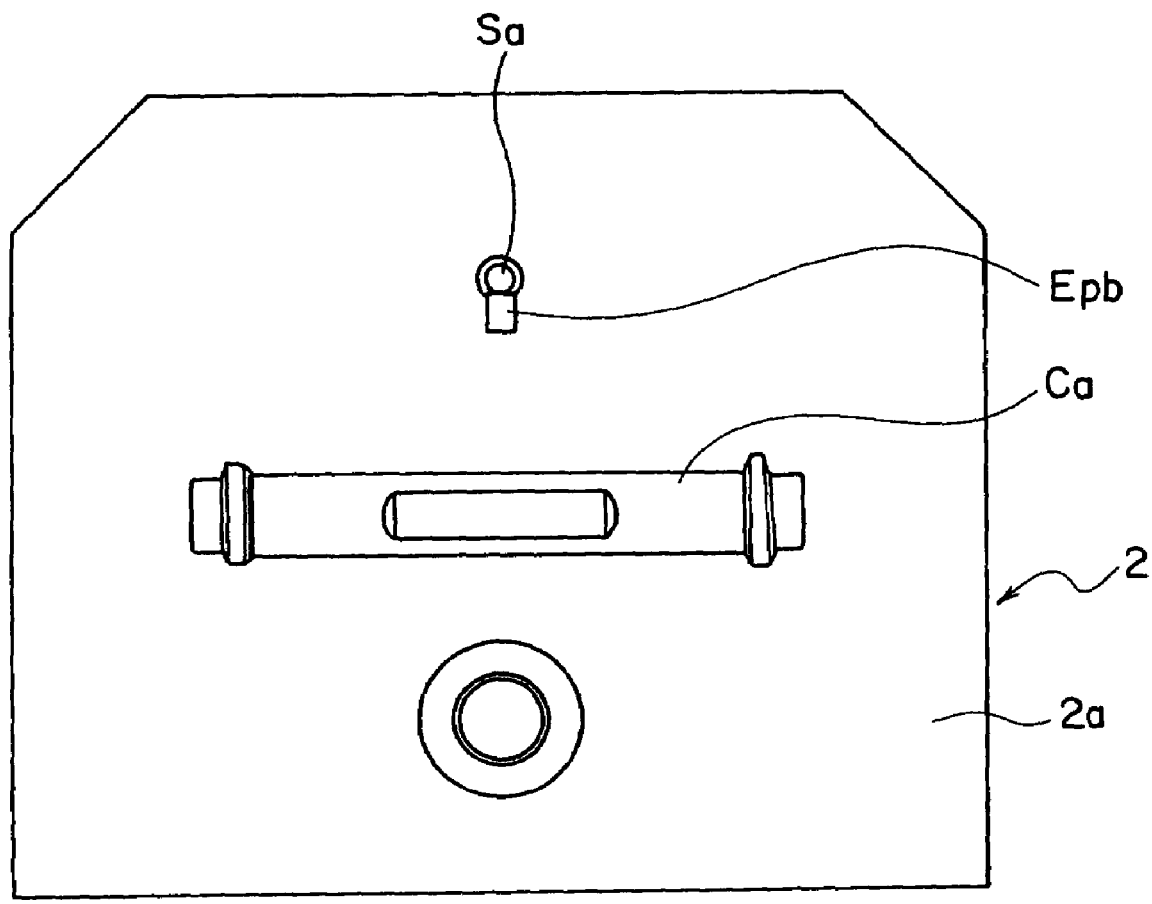
FIG. 4 is a view of the configuration of the parting face of the fixed die.
Figure 5:
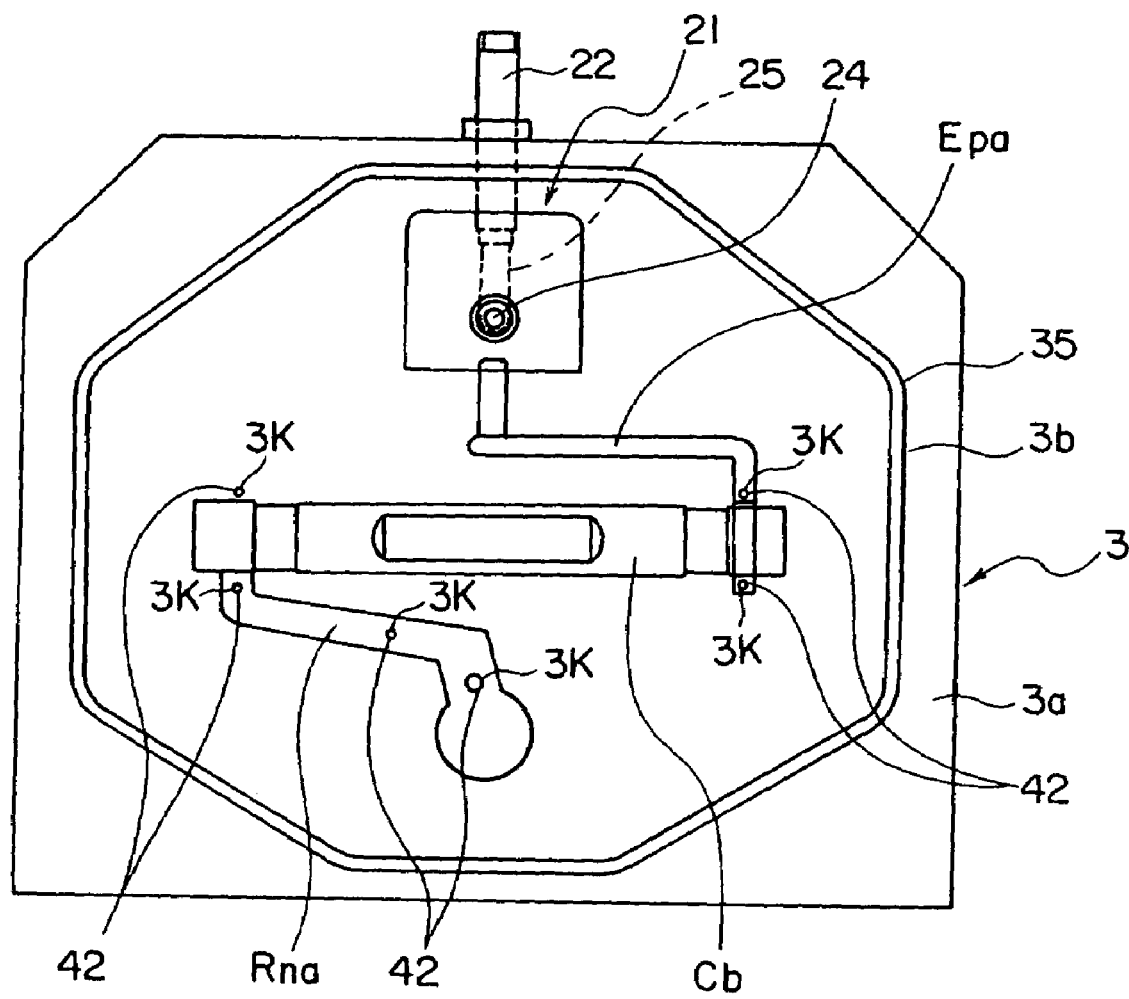
FIG. 5 is a view of the configuration of the parting face of the movable die.

FIG. 3 is a sectional view of the configuration around the dies according to the embodiment of the present invention. Further, FIG. 4 is a view of the configuration of a contact face (parting face) of the fixed die 2, while FIG. 5 is a view of the configuration of a contact face (parting face) of the movable die 3. Note that the fixed die 2 and the movable die 3 shown in FIG. 3 are in a clamped state.

As shown in FIG. 3, the injection apparatus 95 is arranged at the back side of the fixed die 2.

The injection apparatus 95 is provided with a cylindrical sleeve 96 arranged at the back side of the fixed die 2, a plunger tip 97 fit into the inner circumference of this sleeve 96, a plunger rod 98 connected with the plunger tip 97 at its end, and an injection cylinder apparatus 99 connected with the other end of the plunger rod 98.

The sleeve 96 is provided with a supply port 96a. Molten metal ML is supplied into the sleeve 96 through this supply port 96a by a ladle 100.

The injection cylinder apparatus 99 incorporates a piston. A piston rod 99a connected with this piston and the plunger rod 98 are connected by a coupling 99b. This injection cylinder apparatus 99 is driven by hydraulic pressure to extend and retract the piston rod 99a.

The plunger tip 97 is connected to the plunger rod 98 and is moved in the sleeve 96 by a drive operation of the injection cylinder apparatus 99. The movement of the plunger tip 97 in the sleeve 96 supplied with the molten metal ML toward the side of the fixed die 2 causes the molten metal to be filled in the cavity throughout a runner portion Rn formed by the fixed die 2 and the movable die 3.

Note that a sensor 98*a* detects the number of magnetic poles N and S, formed on the periphery of the plunger rod 98 at a predetermined pitch in an axial direction, which are passed as a pulse signal. The injection speed of the plunger tip 97 is detected based on the number of pulses of this pulse signal.

The output of the sensor 98*a* is supplied to a machine controller 52. A current position counter 52*a* in the machine controller 52 detects the position of the plunger tip 97 based on a pulse signal from the sensor 98*a*.

Further, reference numeral 52*b* shows a register for setting a position where the plunger tip 97 passes a molten metal supply port of the sleeve 96, while reference numeral 52*c* shows a register for setting a position to change the injection speed of the plunger tip 97 to a higher injection speed. When the value of the counter 52*a* reaches the value of either of the registers 52*b* and 52*c*, the machine controller 52 issues a valve controller 51 a command to open or shut the valve of a corresponding hydraulic system for driving the plunger tip 97.

The runner portion Rn is formed from channels Rna formed on the parting face 3*a* of the movable die 3 shown in FIG. 5 and the parting face 2*a* of the fixed die 2.

The cavity C is formed from a curved surface Ca formed in the parting face 2*a* of the fixed die 2 shown in FIG. 4 and a curved surface Cb formed in the parting face 3*a* of the movable die 3 shown in FIG. 5 corresponding to the shape of die casting.

As shown in FIG. 3, an evacuation path Ep is formed above the cavity C. This evacuation path is formed from a channel Epa communicated with the curved surface Cb formed in the parting face 3*a* of the movable die 3 shown in FIG. 5 and a channel Epb formed in the face 2*a* of the fixed die 2 shown in FIG. 4. Note that a recess Sa adjoining the channel Epb is a contact portion of a valve described below.

As shown in FIG. 3, a valve mechanism 21 is arranged so as to be communicated with the evacuation path Ep formed between the parting face 2*a* of the fixed die and the parting face 3*a* of the movable die 3.

An explanation will be made of the configuration around this valve mechanism 21 with reference to FIG. 6.

Figure 6:
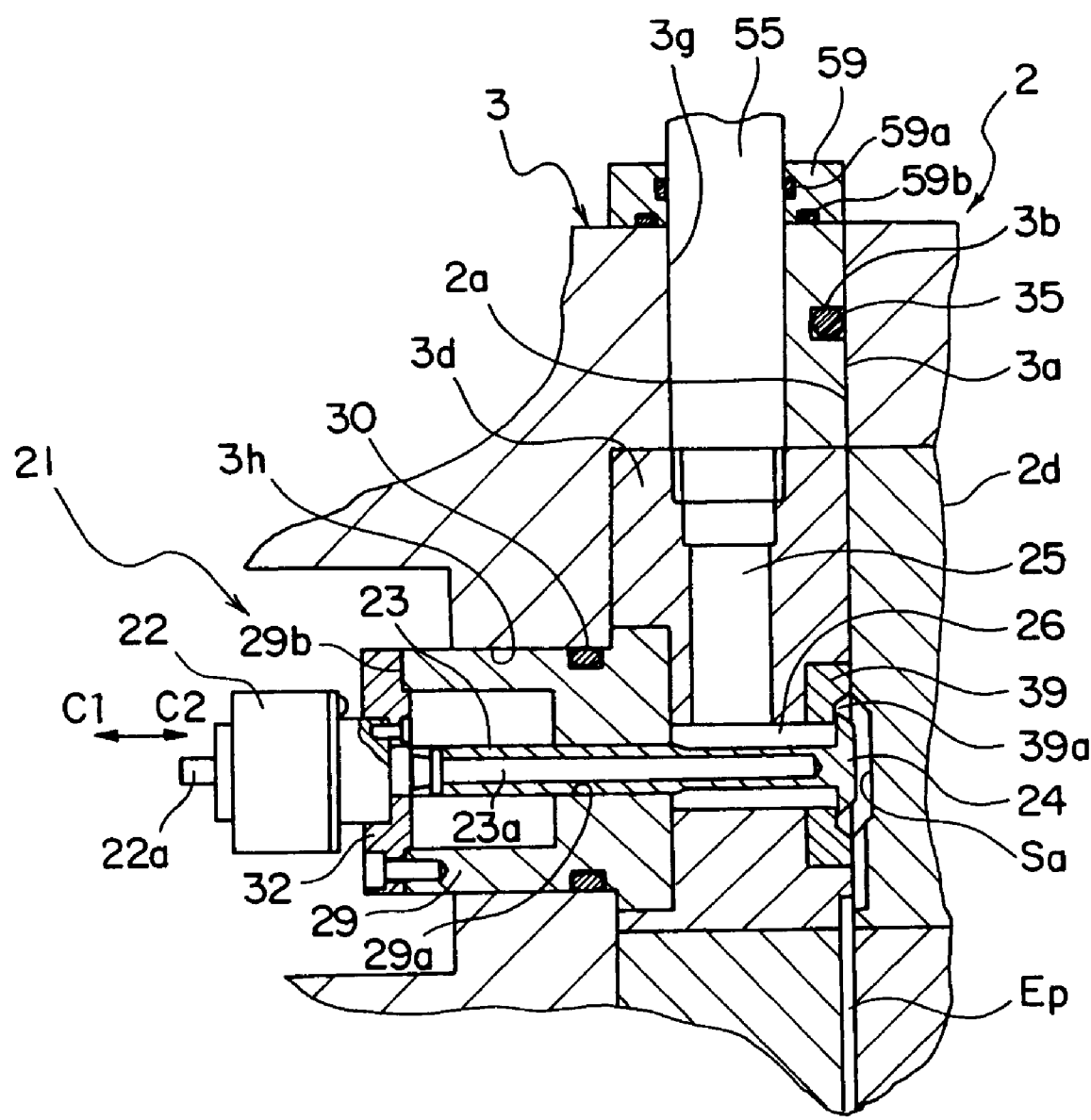
FIG. 6 is a sectional view of the configuration around the valve mechanism 21.

As shown in FIG. 6, the valve mechanism 21 is provided with an electromagnetic actuator 22, a valve shaft connected to the electromagnetic actuator 22, and a disc-shaped valve element 24 formed integrally at the front end of the valve shaft 23.

The valve shaft 23 and the valve element 24 are made of a metal material such as stainless steel.

The electromagnetic actuator 22 is fixed on an opening end 29*b* of a cup-shaped guide member 29 via a flange member 32. The cup-shaped guide member is inserted and tightly fit into an insertion hole 3*h* formed in the movable die 3.

An O-ring made of a plastic is interposed between the guide member 29 and the insertion hole 3*h* formed in the movable die 3 to seal them.

A guide hole 29*a* is formed at the bottom portion of the guide member 29. The valve shaft 23 is movably inserted and tightly fit into this guide hole 29*a*. From the viewpoint of the stability at the time of movement, the portion which fits in the guide hole 29*a* is made larger in diameter than the valve element 24 side. Further, the valve shaft is precisely fit with the guide hole 29*a*, so the space between the guide hole 29*a* and the valve shaft 23 is sealed.

The valve shaft 23 has a hollow portion 23*a* inside. This is to make the speed of movement of the valve shaft 23 higher by lightening the weight and reducing the inertia of the valve shaft 23.

In the movable die 3, an evacuation path 26 communicated with the above evacuation path Ep and for insertion of the valve shaft 23 is formed in a direction vertical to the parting face 3*a* of the movable die 3. Note that the portion of the movable die 3 where the evacuation path 26 is formed is formed by a different metal member 3*d* for assembly of the valve mechanism 21 in the movable die 3.

A valve seat portion 39 is formed at the front end of the evacuation path at the parting face 3*a* side. This valve seat portion 39 faces the valve element 24 and shuts the evacuation path 26 by contact of the valve element 24 with a valve seat 39*a* formed on it. Note that the valve seat 39*a* is formed along the parting face 3*a* of the movable die 3.

This valve seat portion 39 is made of a material which is softer than that of the valve element 24. Specifically, the material is a metal such as a copper alloy.

An evacuation path 25 is formed in the movable die 3 along a direction crossing the evacuation path 26 at right angles. The evacuation path 25 is communicated with the evacuation path 26. An attachment hole 3*g* is formed above this evacuation path 25. An evacuation pipe 55 is inserted in this attachment hole 3*g*.

The evacuation pipe 55 is formed with a thread on the outer circumference at the front end. This thread engages with a thread formed at the inner circumference of the attachment hole 3*g*.

Further, a ring member 59 is fixed around the top end side of the attachment hole 3*g* via O-rings 59*a* and 59*b* made of plastic to seal the space between the evacuation pipe 55 and the attachment hole 3*g*.

The electromagnetic actuator 22 has a shaft member 22*a* connected with the valve shaft 23, a not illustrated permanent magnet fixed to this shaft member 22*a*, and a not illustrated electromagnet arranged around this permanent magnet inside of its case.

By supplying the electromagnet with electric power from the outside, an attraction force occurs between the permanent magnet and the electromagnet so that the shaft member 22*a* is moved linearly.

The electromagnetic actuator 22 drives the valve element 24 in a direction to open or shut the evacuation path 26 as shown by arrows C1 and C2 in FIG. 6 by suitably changing the direction of the current supplied to the electromagnet.

As shown in FIG. 3, this electromagnetic actuator 22 is electrically connected to the valve controller 51 and is supplied with electric power from the valve controller 51.

The valve controller 51 controls the drive operation of the electromagnetic actuator 22 to open or shut the valve element 24. This valve controller 51 is electrically connected to the machine controller 52 generally controlling the die casting machine 1 and controls the electromagnetic actuator 22 in response to a signal input from the machine controller 52.

As shown in FIG. 3, the above evacuation pipe 55 is connected to a vacuum pump 50. This vacuum pump 50 evacuates air in the cavity through the evacuation pipe 55, the evacuation path 25, the evacuation path 26, and the evacuation path Ep. As the vacuum pump, one which can evacuate the cavity to create a high vacuum of several to several tens of Torr is used.

The parting face 3*a* of the movable die 3 is formed with a channel 3*b* in which a sealing member 35 is laid. Part of the sealing member 35 sticks out from the parting face 3*a*.

When the parting face 3a of the movable die 3 contacts the parting face 2a of the fixed die 2, the sticking out portion of the sealing member 35 contacts the parting face and seals between the parting face 2a and the parting face 3a.

Preferably, the sealing member 35 is made of a relatively high heat resistant material such as silicone rubber. Note that a configuration where the sealing member 35 is laid in the parting face 2a can also be employed.

As shown in FIG. 5, the sealing member 35 is arranged continuously at the periphery of the parting face 3a of the movable die 3 without break.

Further, the evacuation path Ep, the cavity C, and the runner portion Rn are arranged inside from the sealing member 35 and are sufficiently away from the sealing member 35.

Next, an explanation will be made of a specific configuration of the ejecting mechanism 41.

As shown in FIG. 3, the ejecting mechanism 41 is arranged at the back side of the movable die 3.

The ejecting mechanism 41 is provided with a plurality of ejecting pins 42, holding plates 43, 44 for holding ends of the ejecting pins 42, a movable plate 45 to which the holding plates 43, 44 are fixed, a guide shaft 46 for movably guiding the movable plate 45 to the movable die 3, and a seal cooling mechanism 61.

The ejecting pins 42 are formed by metal members of stainless steel etc. and are inserted and tightly fit into insertion holes 46 formed in the movable die 3. Note that, as below described, the insertion holes tightly fit with the ejecting pins 42 at only the parts near the parting face 3a of the movable die 3 and are enlarged in diameter at the other parts to allow the pins to easily slide.

As shown in FIG. 5, the insertion holes 3k open at the parting face 3a of the movable die 3. The insertion holes 3k are arranged facing the runner portion Rn, periphery of the cavity, or evacuation path Ep. By extension of the front ends of the ejecting pins 42 from these insertion holes 3k, the die casting stuck in the movable die 3 can be ejected.

The holding plates 43 and 44 grip the enlarged diameter rear ends of the ejecting pins 42. These holding plates 43 and 44 are fixed on the movable plate 45.

As shown in FIG. 3, the movable plate 45 is movably guided in the direction of the arrows E1 and E2. This movable plate 45 is moved by a not illustrated driving means in the direction of the arrows E1 and E2 within a predetermined range. By the movement of the movable plate 45 in the direction of the arrows E1 and E2, the front ends of the ejecting pins 42 protrude from the parting face 3a of the movable die 3.

The ejecting pins 42 tightly fit with the insertion holes 3k, so there is no possibility that the molten metal will invade a space between the ejecting pins 42 and the insertion holes 3k, but there is possibility that air will enter between the ejecting pins 42 and the insertion holes 3k. If air can enter between the ejecting pins 42 and the insertion holes 3k, it will be impossible to make the cavity a high vacuum when reducing the pressure in the cavity.

Further, because the ejecting pins 42 directly contact the high temperature die casting, there is possibility that the temperature of the ejecting pins 42 will also become high. Therefore, when sealing the spaces between the ejecting pins 42 and the insertion holes 3k with sealing members (O-rings) made of plastic, there is a possibility that the O-rings will not be able to endure the high temperature and therefore continuous use of the O-rings will become impossible.

In the present embodiment, in order to solve the above problem, a seal cooling mechanism is arranged at the back side of the movable die 3.

Figure 7:
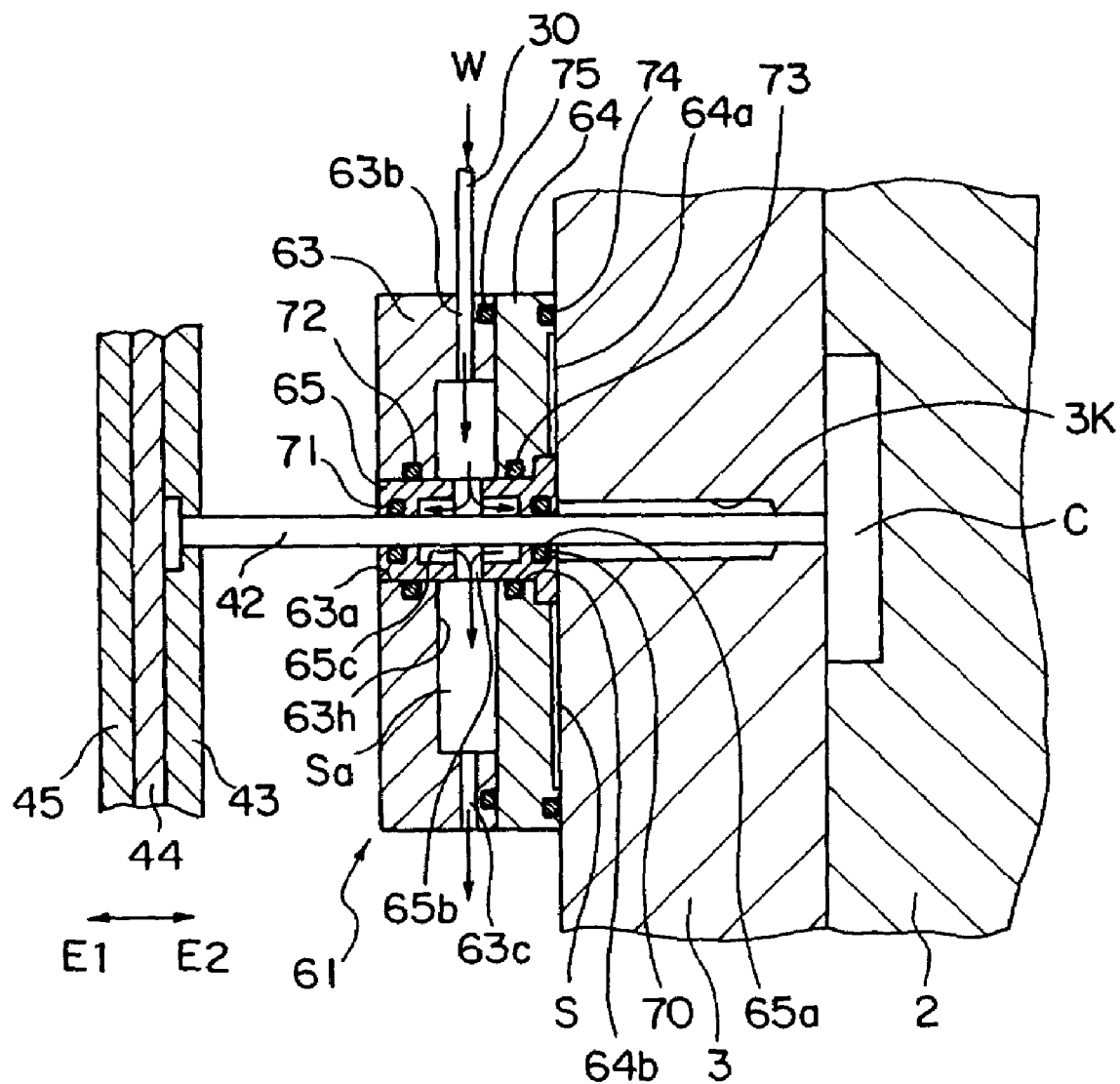
FIG. 7 is a sectional view of the concrete configuration of the seal cooling mechanism 61.

FIG. 7 is a view of a concrete configuration of the seal cooling mechanism 61.

As shown in FIG. 7, the seal cooling mechanism 61 has a plate-shaped first member 63 having a recess 63h, a plate-shaped second member 64 fixed to the first member 63 at the recess 63h side, and a seal holding member 65 (only one shown) fixed to the first member 63 and the second member 64. Note that here, while only one seal holding member 65 is shown and the explanation is given of only one such member, in practice there are a plurality of members corresponding to the number of ejecting pins.

The first member 63 is fixed to the second member to form a coolant storage space Sa comprised of the recess 63h of the first member 63 and the opposing face of the second member 64. Between the first member 63 and the second member 64 is interposed an O-ring 75 made of plastic to seal the first member 63 and the second member 64.

The second member 64 is fixed to the back face of the movable die 3. A plastic O-ring 74 is interposed at the periphery between the second member 64 and the back face of the movable die 3 to seal the second member 64 and the back face of the movable die 3.

A recess 64a is formed in the surface of the second member 64 facing the movable die 3 positioned at the inside of the O-ring 74. A space S is formed between the movable die 3 and the second member 64.

A supply port 63b for supplying the coolant storage space Sa with a coolant W and an outlet 63c for discharging the coolant W are formed in the peripheral wall of the first member 63.

The seal holding member 65 is formed of a cylindrical member and has an enlarged diameter at the end at the back side of the movable die 3. Further, the seal holding member 65 is inserted and tightly fit at its outer circumference into an insertion hole 63a formed in the first member 63 and an insertion hole 64b formed in the second member 64 so as to be fixed to the first member 63 and the second member 64. O-rings 72 and 73 made of plastic are held at the inner circumferences of the insertion hole of the first member 63 and the insertion hole 64b of the second member 64.

These O-rings 72 and 73 seal the outer circumference of the seal holding member 65 and the insertion hole 63a and the outer circumference of the seal holding member 65 and the insertion hole 64b.

The seal holding member 65 is provided with a through hole 65a in the center into which an ejecting pin 42 is inserted and tightly fit. An O-ring made of plastic is held at the inner circumference of this through hole 65a at the second member 64 side, while an O-ring 71 made of plastic is held at the inner circumference at the first member 63 side.

The O-rings 70, 71 seal the ejecting pin 42 and the through hole 65a.

Further, the seal holding member 65 is provided with a hollow portion 65c and a through hole 65b formed in the direction crossing the ejecting pin 42 at right angles.

In the above seal cooling mechanism 61, the supply port 63b of the first member 63 is connected with a coolant supplying pipe 30. A coolant W is supplied to the seal cooling mechanism 61 through the coolant supplying pipe 30. As the coolant W, water for example can be used.

The coolant supplied from the coolant supplying pipe 30 is introduced into the coolant storage space Sa. Part of the coolant W is supplied to the hollow portion 65b through the through hole 65b of the seal holding member 65.

The coolant supplied to the hollow portion 65b cools the part of the ejecting pin 42 exposed at the hollow portion 65c.

Accordingly, the ejecting pin 42 in the vicinity of the hollow portion 65c is partially cooled. By continuously supplying the coolant W from the coolant supplying pipe 30, fresh coolant is circulated around the hollow portion 65c and discharged to the outlet 63c through the through hole 65b.

On the other hand, out of the O-ring 70 and O-ring 71 which tightly fit with the outer circumference of the ejecting pin 42, the O-ring 70 functions to prevent air from entering from outside to between the insertion hole 3k formed in the movable die 3 and the ejecting pin 42 and to prevent the coolant W from entering into the insertion hole 3k. The O-ring 71 functions to prevent the coolant from leaking outside from the coolant storage space Sa.

If these O-rings 70 and 71 were formed of a heat resistant material such as silicone rubber or a fluororubber, the O-rings 70 and 71 would not be able to endure continuous use under an environment where the ejecting pin 42 reaches a high temperature such as over 200° C.

In this embodiment, therefore, even if the temperature of the ejecting pin 42 rises by contact of the ejecting pin 42 with a high temperature die casting, because a hollow portion 65c is arranged around the O-rings 70, 71, the temperature of the part of the ejecting pin 42 contacting the O-rings 70 and 71 is kept below 100□C. As a result, the O-rings 70 and 71 are not damaged by heat.

Next, an explanation will be made of an example of the operation of the above die casting machine 1.

First, from the state of the die casting machine 1 shown in FIG. 2, that is, from the state where the movable die 3 is opened from the fixed die 2, the machine controller 52 operates the toggle die clamping mechanism 110 to clamp the fixed die 2 and the movable die 3.

By clamping the fixed die 2 and the movable die 3, the sealing member 35 seals the parting face 2a of the fixed die 2 and the parting face 3a of the movable die 3.

At the time of startup of the die casting machine 1, the above seal cooling mechanism 61 is already supplied with the coolant W.

Further, at the time of startup of the die casting machine 1, the vacuum pump is also started, but the valve element 24 of the valve mechanism 21 shuts the evacuation path 26. Therefore, the cavity is not evacuated.

On the other hand, the sleeve 96 of the injection apparatus 95 is supplied with a predetermined amount of molten metal such as aluminum alloy by the ladle 100.

When the ladle 100 finishes supplying the molten metal, the plunger tip 97 is driven under the control of the machine controller 52. When the front end of the plunger tip 97 passes the supply port 96a of the sleeve 96, the sleeve is sealed by the plunger tip 97 to cut off entry of air to the cavity C from the sleeve 96 side.

Note that the plunger tip 97 is driven normally at a low speed when starting to move the plunger tip 97.

The machine controller 52 judges when the plunger tip 97 has passed the supply port 96a of the sleeve 96 and outputs a command to open the valve element 24 of the valve mechanism 21 to the valve controller 51.

Receiving the command from the machine controller 52, the valve controller 51 supply electric power for driving the electromagnetic actuator 22 of the valve mechanism 21 to the electromagnetic actuator.

Figure 8:
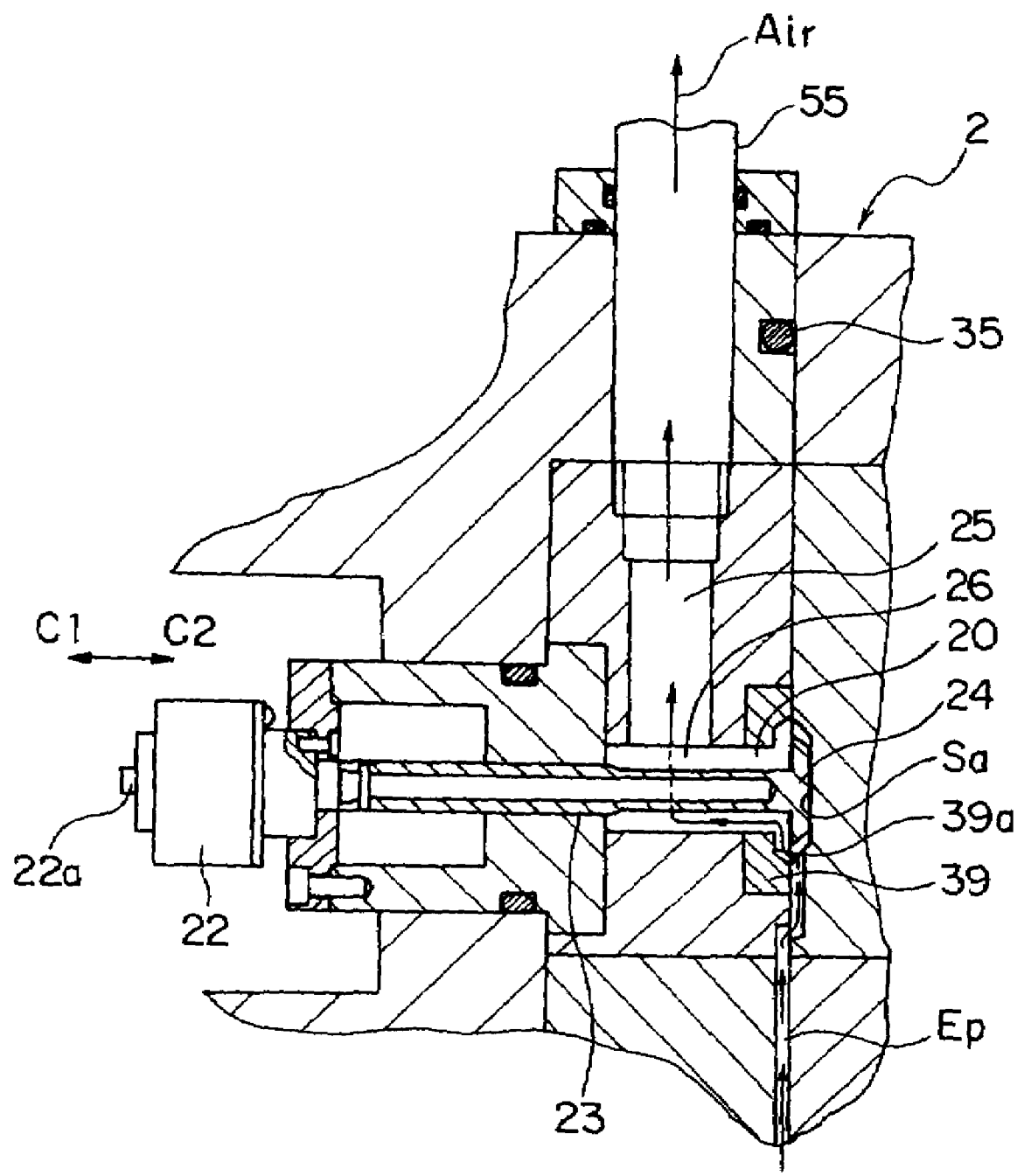
FIG. 8 is a view for explaining the operational state of the valve mechanism 21.

When the electromagnetic actuator 21 is driven, as shown in FIG. 8, the valve element 24 is moved in the direction of the arrow C2, contacts a contact face Sa formed at the parting face 2a of the fixed die 2, and stops.

At this time, because the valve element 24 is driven by the electromagnetic actuator 22, it takes a substantially constant time of more than several ms or less than 20 ms to open the valve element 24. For example, in case of using a hydraulic cylinder to drive the valve element 24, it takes 200 some odd milliseconds until the valve element 24 is completely opened. Further, this time is uneven.

By this movement of the valve element 24, a space is formed between the valve element 24 and the valve seat 39a. Air (gas) in the cavity is evacuated from this space between the valve element 24 and the valve seat 39a through the evacuation path Ep communicated with the cavity C, the evacuation path 26, the evacuation path 25, and the evacuation pipe 55.

The sealing member 35 seals reliably the parting face 2a of the fixed die 2 and the parting face 3a of the movable die 3. Further, because the O-rings 70 arranged at the seal cooling mechanism 61 reliably seal the ejecting pins 42 and the movable die 3, the pressure in the cavity is rapidly reduced.

Here, an explanation will be made of the relation between the pressure reduction in the cavity and the injection speed with reference to the graph shown in FIG. 9.

Figure 9:
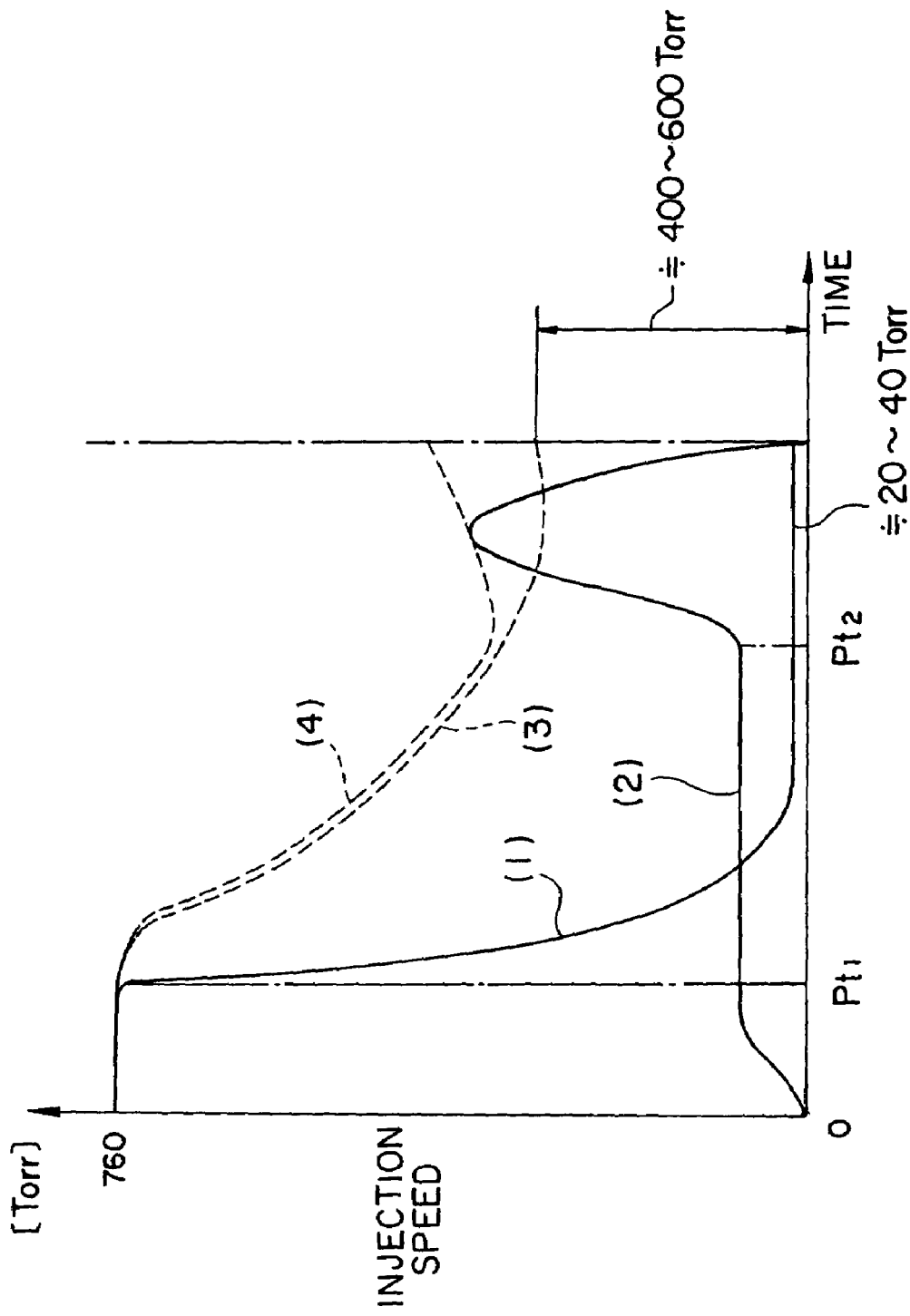
FIG. 9 is a view for explaining the relationship between the reduced pressure and the injection speed in the cavity.

The curve (1) shown in FIG. 9 shows the pressure reduction in the cavity. The curve (2) shows the injection speed of the plunger tip 97. Note that the curve (3) shows a comparative example of pressure reduction in a cavity when operating a valve using a conventional solenoid valve and hydraulic or air cylinder apparatus. The curve (4) shows the pressure reduction in the cavity when closing an evacuation path by driving a valve with inertia of molten metal injected and filled in the cavity. The curves (3) and (4) show the pressure reduction in a die casting machine not provided with the seal cooling mechanism 61 and the continuous sealing member between the parting face 2a of the fixed die 2 and the parting face 3a.

As shown by the curve (1), if the time of start of pressure reduction is pt1, because of the good response of the valve element 24, the pressure in the cavity is rapidly reduced from the pressure reduction start time pt1. Further, because there is almost no leakage of air between the ejecting pins and the die or between the parting face 2a of the fixed die 2 and the parting face 3a of the movable die 3, it is understood that the pressure in the cavity is efficiently reduced in a short time.

On the other hand, in the curve (3) or the curve (4), because of using a cylinder apparatus to drive the valve, the time lag from the pressure reduction start time pt1 until the pressure reduction actually starts is relatively long and there is leakage of air from between the ejecting pins and the die or between the parting face 2a of the fixed die 2 and the parting face 3a of the movable die 3. Therefore, the pressure in the cavity is not efficiently reduced.

Along with movement of the plunger tip 97, the runner portion Rn communicating with the cavity C and the sleeve 96 is also filled with the molten metal ML. In this state, the cavity becomes a high vacuum of about 20 to 40 Torr.

The molten metal is injected into and fills the cavity by changing the injection speed of the plunger tip 97 to a high speed. That is, the injection speed is changed to a high speed at the high speed injection start time pt2.

However, it is necessary to shut the evacuation path by the valve element 24 to prevent the molten metal ML from intruding into the valve mechanism 21 before changing to high speed injection.

Preferably, the timing for shutting the evacuation path 26 by the valve element 24 is immediately before the high speed injection start time pt2. That is, this is because there is possibility that after shutting the evacuation path 26 by the valve element 24, the cavity C will not be evacuated and the pressure in the cavity will rise due to leakage of air.

In the present embodiment, however, because of using the electromagnetic actuator 22 for driving the valve element 24 and making the valve shaft 23 light in weight, it is possible to shut the evacuation path 26 in a short time of as much as several ms to less than 20 ms. Further, because there is almost no unevenness of the response of the electromagnetic actuator 22, it becomes possible to inject the molten metal into the cavity immediately before the high speed injection start time pt2.

Note that the timing for shutting the evacuation path 26 by the valve element 24 is determined by the machine controller 52 based on the detected position of the plunger tip 97 and the detected pressure in the cavity. The machine controller 52 outputs a command to the valve controller 51 in response to these position signal and pressure signal.

When driving the electromagnetic actuator 22 and shutting the evacuation path 26 by the valve element 24, there is possibility that the valve element 24 will rebound and jump up because it strikes the valve seat 39a of the valve seat portion 39 at a high speed.

However, in the present embodiment, it is possible to suppress the jump of the valve element 24 when the valve element 24 strikes the valve seat portion 39, because of use of a material suppressing rebound to form the valve seat portion 39, that is, a softer material than the valve element 24. As a result, it is possible to prevent the molten metal from intruding into the valve mechanism 21 by mistake.

When changing to the high speed injection at the high speed injection start time pt2, the molten metal ML is filled in the cavity C and then solidified. Due to this, a desirable die casting can be obtained.

In order to eject the formed die casting from the fixed die 2 and the movable die 3 clamped together, the toggle die clamping mechanism is operated to open the movable die 3 from the fixed die.

When the movable die 3 is opened from the fixed die 2 (at this time, the plunger tip is pushing a biscuit following the runner portion Rn), the formed die casting is separated from the fixed die 2.

By operating the ejecting mechanism 41 in this state to extend the ejecting pins 42 from the parting face 3a of the movable die 3, it becomes possible to eject the die casting from the movable die 3.

At this time, because the ejecting pins 42 directly touch the high temperature die casting, the temperature of the ejecting pins 42 also rises.

The seal cooling mechanism 61 partially cools the ejecting pins 42, so the O-rings 70 and 71 are not exposed to a high temperature and the function of the O-rings 70 and 71 is not damaged by heat.

Further, the seal cooling mechanism 61 is continuously supplied with the coolant W, so the temperature of the seal cooling mechanism 61 falls sufficiently compared with the temperature of the movable die 3.

Due to this, if the seal cooling mechanism 61 were to directly contact the movable die 3, the temperature distribution of the movable die 3 might be influenced and the quality of the die casting might fall. In the present embodiment, however, because a space is formed between the seal cooling mechanism 61 and the movable die 3, the seal cooling mechanism 61 does not directly contact to the movable die 3 and it becomes possible to keep the seal cooling mechanism 61 from affecting the movable die 3.

As described above, according to the present embodiment, by using the electromagnetic actuator 22 to drive the valve element for opening and shutting the evacuation path communicating the cavity C and the vacuum pump, it becomes possible to rapidly open and shut the evacuation path. Because the electromagnetic actuator 22 is driven by electric power, it is not necessary to supply an operating fluid and it becomes possible to make the valve mechanism 21 compact. Due to this, the freedom of arrangement of the valve mechanism 21 with respect to the dies increases so that it becomes easy to optimize the arrangement of the valve element and the evacuation path communicating between the cavity C and the vacuum pump.

Because the arrangement of the evacuation path communicating the cavity C with the vacuum pump 50 can be optimized, it becomes possible to interpose the sealing member 35 between the peripheries of the parting face 2a of the fixed die 2 and the parting face 3a of the movable die 3 without break, secure fully the distance between the evacuation path communicating the cavity C with the vacuum pump 50 and the sealing member 35, and prevent the sealing members from being damaged by heat.

Further, according to the present embodiment, by partially force-cooling the ejecting pins liable to rise to a high temperature, general use sealing members such as O-rings can be easily used to seal between the ejecting pins 42 and the die.

Second Embodiment

Figure 10:
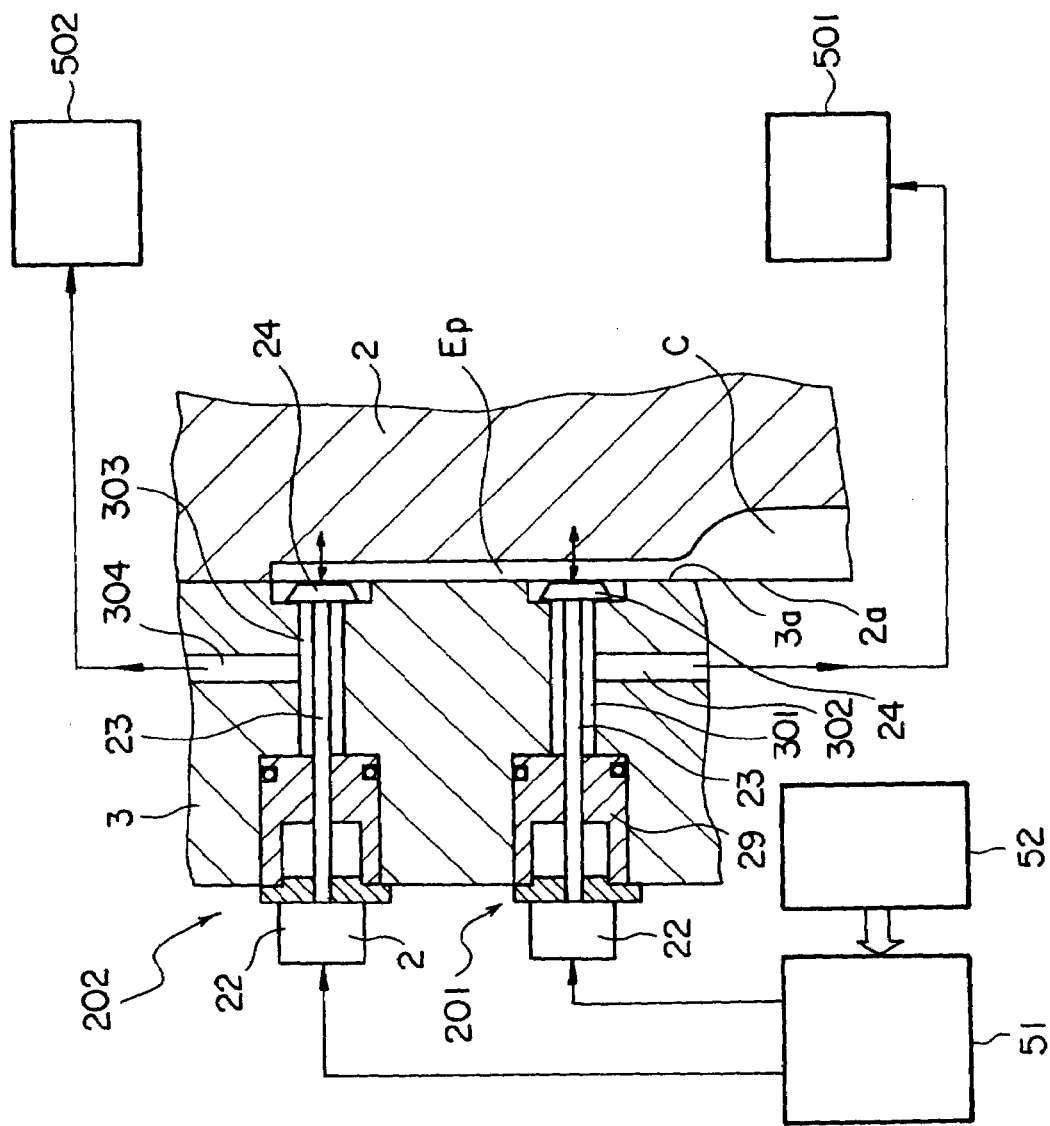
FIG. 10 is a sectional view of the configuration around the dies according to the second embodiment of the present invention.

FIG. 10 is a sectional view of the configuration around the dies of a second embodiment of a die casting machine according to the present invention. In FIG. 10, the same reference numerals are used for the same parts of the above described embodiment.

As shown in FIG. 10, a plurality of valve mechanism 201 and 202 are arranged at the movable die of the die casting machine.

The configuration of the valve mechanisms 201 and 202 is the same as that of the above valve mechanism 21.

The valve mechanisms 201 and 202 are arranged in the middle of the evacuation path Ep formed between the parting face 3a of the movable die 3 and the parting face 2a of the fixed die 2. The evacuation path is communicated with the cavity C.

The evacuation path Ep is communicated with a vacuum pump 501 via evacuation paths 301 and 302 formed corresponding to the valve mechanism 201 and is communicated with a vacuum pump 502 via evacuation paths 303 and 304 formed corresponding with the valve mechanism 202 in the movable die 3.

The vacuum pump 501 is provided with an evacuation ability equal to that of the vacuum pump 502.

The electromagnetic actuators 22 of the valve mechanisms 201 and 202 are connected commonly with the valve controller 51.

This valve controller 51 can drive the valve mechanisms 201 and 202 independently.

As described above in the first embodiment, by using the electromagnetic actuator 22 to drive a valve element 24, it becomes possible to make the valve mechanism more compact and increase the freedom of the arrangement with respect to the die.

Due to this, it is possible to easily arrange the valve mechanisms with respect to the die.

As mentioned above, by arranging the plurality of valve mechanisms 201 and 202 at the die, it becomes possible to enlarge the total sectional area of the evacuation path for evacuation compared with the case of arranging a single valve mechanism with respect to the die. Therefore, it becomes possible to efficiently evacuate the cavity C. That is, when arranging a single valve mechanism at the die, even if the evacuation ability of the vacuum pump is enhanced, it is not possible to rapidly reduce the pressure in a short time because the sectional area of the evacuation path is small. By arranging a plurality of valve mechanisms 201 and 202 at the die and enabling the valve mechanisms 201 and 202 to be independently driven, it becomes possible to optimize the opening and shutting timings of the valves in accordance with the arrangement of the valve mechanisms.

Next, an example will be made of the pressure reduction operation in the cavity C in the case of using the plurality of valve mechanism with reference to FIG. 11.

Figure 11:
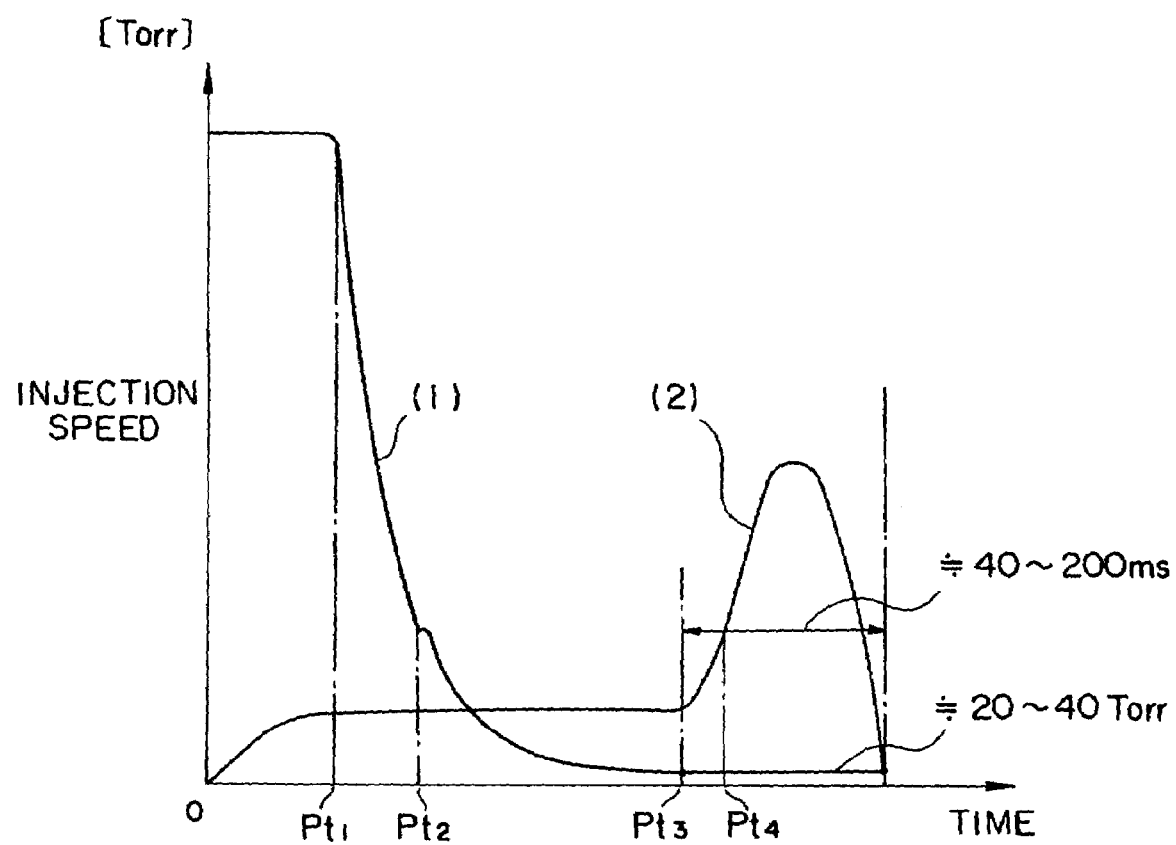
FIG. 11 is a view for explaining the relationship between the reduced pressure and the injection speed in the cavity.

In FIG. 11, the curve (1) shows the pressure reduction in the cavity, while the curve (2) shows the injection speed of the plunger tip 97.

First, the movement of the plunger tip 97 is started at a low speed from the state with the evacuation path shut by the valve mechanisms 201 and 202.

Next, at the injection start time Pt1, the valve mechanism 201 is opened and the pressure in the cavity C starts to be reduced. Note that the other valve mechanism 202 is shut in this state.

By opening the valve mechanism 201, the pressure in the cavity C is rapidly reduced by the vacuum pump 501.

Next, when reaching the time Pt2 where the pressure in the cavity is reduced to some degree, the valve mechanism 201 is shut and the valve mechanism 202 is opened. By this, the reduction of the pressure in the cavity C is continued by the vacuum pump 502. These opening and shutting operations of the valve mechanisms 201 and 202 are made by outputting command from the machine controllers 52 to the valve controller 51.

Note that as a characteristic of a vacuum pump, it is known that the evacuation speed gradually decreases along with a reduction of the pressure. For example, when the pressure is reduced by the vacuum pump 501, the evacuation speed gradually falls. Due to this, by changing the vacuum pump for reducing the pressure in the cavity C to the vacuum pump 502 after the reduction of pressure by the vacuum pump 501 progresses to some extent, it becomes possible to suppress the decrease of the evacuation speed as much as possible and shorten the time required to reduce the pressure to a desirable pressure.

By reducing the pressure in the cavity by the vacuum pump 502, the cavity reaches in a high vacuum.

In this state, as shown at the time Pt3 of the curve (2), the injection speed of the plunger tip 97 is changed to a high speed.

On the other hand, from the viewpoint of maintaining the cavity at a high vacuum, it is preferable that the timing to shut the valve mechanism 202 be as late as possible. Accordingly, even after changing to high speed injection, by leaving the valve mechanism 202 open so long as the molten metal does not reach the valve mechanism 202, it becomes possible to reliably suppress the rise of the pressure in the cavity C after shutting the evacuation path communicated with the vacuum pump 502.

In the present embodiment, the valve mechanism 202 is shut after changing to high speed injection as at the time Pt4 in the curve (2).

The time required for the high speed injection is short such as for example 40 ms to 200 ms. In the present embodiment, because of using the electromagnetic actuator 22 in the valve mechanism, it becomes possible to shut the valve mechanism 202 timely in such a limited time.

Further, the valve mechanism 202 is located away from the cavity C compared with the valve mechanism 201. By shutting the valve mechanism 202 located apart like this last, it becomes possible to prevent the molten metal from entering into the valve mechanism while delaying the timing to shut the evacuation path communicated with the cavity C as much as possible.

Summarizing the effects of the invention, as described above, according to the present invention, it is possible to provide a die casting machine using vacuum casting which can realize a high vacuum in the cavity.

Further, according to the present invention, it becomes possible to efficiently reduce the pressure in the die cavity in short time.

While the invention has been described with reference to specific embodiment chosen for purpose of illustration, it should be apparent that numerous modifications could be made thereto by those skilled in the art without departing from the basic concept and scope of the invention.

What is claimed is:

1. A die casting machine for forming a product, comprising:
   a fixed die;
   a movable die movably positioned to face the fixed die and to cooperate with the fixed die to define a cavity in which the product is formed;
   an injection apparatus configured to inject molten metal into the cavity;
   a vacuum pump configured to reduce pressure in the cavity and in a path of the molten metal in communication with the cavity;
   an ejection mechanism configured to fix to the movable die, the ejection mechanism comprising at least one ejecting pin and a seal holding member, the ejection mechanism being configured to define a first coolant accommodating space,
      wherein the seal holding member
         defines a fitting hole in which the ejecting pin is moveably fitted, the fitting hole being in communication with an insert hole formed in the movable die to the cavity,
         has a first O ring arranged at an inner wall of the fitting hole in contact with the ejecting pin at a first side of the seal holding member adjacent to the insert hole of the movable die,
         has a second O ring at the inner wall of the fitting hole in contact with the ejecting pin at a second side of the seal holding member opposite to the first side, and
         defines a second coolant accommodating space communicating with the first coolant accommodating space, the ejecting pin penetrating the second coolant accommodating space, the second coolant accommodating space being positioned adjacent to the first and second O rings, and wherein the ejecting mechanism,
         defines a first path introducing coolant into the first coolant accommodating space and a second path discharging the coolant from the first coolant accommodating space, and
         includes an ejection pin movement mechanism configured to move the ejecting pin in the fitting hole and in the insert hole;

a coolant supply configured to supply the coolant into the first coolant accommodating space through the first path; and a coolant discharge configured to remove the coolant from the first coolant accommodating space through the second path.

2. The die casting machine according to claim 1, wherein the ejection mechanism comprises:

a first member and a second member fixed to the movable die to define the first coolant accommodating space therebetween, the seal holding member being positioned between the first and second members;

a third O ring to maintain a seal between the movable die and the second member; and a fourth O ring to maintain a seal between the first and second members.

3. A die casting machine as set forth in claim 1, wherein a space for preventing conductance of heat is formed between said ejection mechanism and said movable and fixed dies.

4. A die casting machine as set forth in claim 1, wherein said ejection mechanism further comprises:

a first plate-shaped member having a recess, a second plate-shaped member fixed to the first plate-shaped member, and a seal holding member fixed to the first and second plate-shaped members.

* * * * *